(12) United States Patent
Nazarova et al.

(10) Patent No.: US 8,815,218 B2
(45) Date of Patent: Aug. 26, 2014

(54) COSMETIC OR DERMATOLOGICAL PREPARATION

(75) Inventors: Daria Nazarova, Hamburg (DE); Jessica Scholze, Winsen (DE); Jan Jänichen, Hamburg (DE); Wilfried Petersen, Hamburg (DE); Manuela Salmina-Petersen, Hamburg (DE)

(73) Assignee: Dr. Straetmans GmbH, Hamburg (DE)

( * ) Notice: Subject to any disclaimer, the term of this patent is extended or adjusted under 35 U.S.C. 154(b) by 0 days.

(21) Appl. No.: 13/265,215

(22) PCT Filed: Apr. 16, 2010

(86) PCT No.: PCT/EP2010/002356
§ 371 (c)(1),
(2), (4) Date: Feb. 9, 2012

(87) PCT Pub. No.: WO2010/121759
PCT Pub. Date: Oct. 28, 2010

(65) Prior Publication Data
US 2012/0128610 A1    May 24, 2012

(30) Foreign Application Priority Data

Apr. 20, 2009  (EP) ..................................... 09005531

(51) Int. Cl.
| | | |
|---|---|---|
| *A61K 8/00* | (2006.01) | |
| *A61K 8/49* | (2006.01) | |
| *A61K 8/29* | (2006.01) | |
| *A61K 8/44* | (2006.01) | |
| *A61K 8/37* | (2006.01) | |
| *A61K 8/35* | (2006.01) | |
| *A61K 8/27* | (2006.01) | |
| *A61Q 17/04* | (2006.01) | |

(52) U.S. Cl.
CPC .............. *A61Q 17/04* (2013.01); *A61K 8/4966* (2013.01); *A61K 8/29* (2013.01); *A61K 8/445* (2013.01); *A61K 8/37* (2013.01); *A61K 8/35* (2013.01); *A61K 8/27* (2013.01)
USPC ........................................... 424/59; 424/70.9

(58) Field of Classification Search
None
See application file for complete search history.

(56) References Cited

U.S. PATENT DOCUMENTS

| | | | | |
|---|---|---|---|---|
| 3,052,607 A * | 9/1962 | Hirsh | ............................ | 514/552 |
| 6,881,776 B2 * | 4/2005 | Butuc | ............................ | 524/284 |
| 7,101,427 B2 * | 9/2006 | Dransfield et al. | ............ | 106/401 |

FOREIGN PATENT DOCUMENTS

| | | |
|---|---|---|
| CN | 1805902 A | 7/2006 |
| DE | 19703471 | 8/1998 |
| DE | 19712033 A1 | 9/1998 |
| DE | 10 2007 017440 | 10/2008 |
| EP | 0693471 B1 | 1/1996 |
| EP | 0775698 B1 | 5/1997 |
| EP | 0860164 B1 | 8/1998 |
| EP | 1859779 | 11/2007 |
| EP | 1807120 B1 | 2/2008 |
| JP | 2005306844 A | 11/2005 |
| WO | 2004/108599 A1 | 12/2004 |

OTHER PUBLICATIONS

Sunscreen, available online 2009.*
EPO Machine Translation of EP 0860164 B1 Description, Published Aug. 26, 1998, translation retrieved on Jan. 5, 2012.
EPO Machine Translation of EP 0693471 B1 Description, Published Jan. 24, 1996, translation retrieved on Jan. 5, 2012.
EPO Machine Translation of DE 10 2007 017440 Description, Published Oct. 16, 2008, translation retrieved on Jan. 10, 2012.
EPO Machine Translation of DE 19703471 Description, Published Aug. 6, 1998, translation retrieved on Jan. 10, 2012.
EPO Machine Translation of EP 0775698 B1 Description, Published May 28, 1997, translation retrieved on Jan. 5, 2012.
EPO Machine Translation of EP 1859779 Description, Published Nov. 28, 2007, translation retrieved on Jan. 10, 2012.
EPO Machine Translation of FR2877570 A1 corresponding to EP 1807120 A1, Published May 12, 2006, translation retrieved on Jan. 5, 2012.
Lochhead, et al., "Encyclopedia of Polymers and Thickeners for Cosmetics", Cosmetics & Toiletries, vol. 108, Allured Publishing Corp., (May 1993), pp. 95.
Rigano et al., "The Miracle question: A new approach to the maze of oil phases," Soaps, Oils, Fats, Waxes Journal, 2004, 130: 1-2, pp. 12-23.
"Emollients in Personal Care for Solubilizing Organic UV Absorbers", IP.com Journal., IP.com inc., West Henrietta, NY, US, Feb. 22, 2006.
EPO Machine Translation of DE 19703471Description, Published Sep. 24, 1998, translation retrieved on Feb. 22, 2012.
English Abstract of JP2005306844, retrieved Sep. 18, 2013, 1 page.
International Publication No. WO 2004/108599 , published Dec. 16, 2004 is the English equivalent of CN 1805902 A.

* cited by examiner

*Primary Examiner* — Anand Desai
*Assistant Examiner* — Melissa Mercier
(74) *Attorney, Agent, or Firm* — Casimir Jones, S.C.

(57) ABSTRACT

The invention relates to a cosmetic or dermatological preparation, comprising: a) one or more chemical light protection filters selected from the group consisting of 2,4,6-Trianilino-p-(carbo-2'-ethylhexyl-1'oxy)-1,3,5-triazine (ethylhexyl triazon), 1-(4-tert-butylphenyl)-3-(4-methoxyphenyl)-propane-1,3-dion (butyl methoxydibenzoyl-methane), bisoctyloxyphenol-methoxyphenyl-triazine (bis-ethylhexyloxyphenol methoxyphenyl triazine) and 2-[-4-(diethylamino)-2-hydroxybenzoyl]benzoic acid hexylester (diethylamino hydroxybenzoyl hexyl benzoate); and/or one or more light protection filters selected from the group consisting of superficially treated, or untreated, pigments of titanium dioxide or zinc oxide; b) at least one ester of a C8-C16-fatty acid and isoamyl alcohol.

12 Claims, No Drawings

COSMETIC OR DERMATOLOGICAL PREPARATION

The present application is a §371 U.S. National Entry of International Patent Application Serial Number PCT/EP2010/002356, filed Apr. 16, 2010, which claims the benefit of European Patent Application Serial Number 09 005 531.0, filed Apr. 20, 2009.

The invention relates to cosmetic or dermatological preparations such as sunscreen preparations, for example.

Protecting the human skin from harmful UV rays has increasingly gained in importance not only as a result of the rising depletion of the ozone layer is some parts of the globe, but also because of the leisure time behavior of people over the past years.

While the short-wave UV range of <290 nm is normally absorbed by the atmospheric ozone layer, the longer-wave UV-B rays having a wavelength of 290-320 nm as well as UV-A rays having a wavelength of 320-400 nm reach the surface of the Earth relatively unimpaired and can cause temporary as well as lasting damage, depending on the exposure duration and frequency of the skin. Even short-term exposure to UV radiation of approximately 310 nm, for example, quickly results in painful sunburns, while longer exposure to longer-wave UV-A radiation can cause phototoxic reactions in the deeper skin layers and causes the skin to age more quickly by damaging the connective tissue. However, not only can the skin's appearance suffer upon extensive UV exposure, malignant cell changes, associated with the formation of melanomas, are also attributed to UV-induced damage to the genetic material of the skin cells.

Sun protection products thus play an important role in keeping the skin healthy.

Modern sun protection products employ filter systems able to absorb or reflect UV rays on the skin surface. A person skilled in the art knows that a differentiation can be made between chemically and physically acting UV filters. The operating principle of chemical UV filters is based on these being able to absorb energy-rich UV radiation and to transition into an excited state. From this excited state, the excited species then relax, while incrementally releasing the absorbed energy, and return to the base state thereof.

Physically acting UV filters, which are based on inorganic pigments such as $TiO_2$ or ZnO, in contrast reflect the UV radiation and thereby prevent the penetration thereof into the skin. Because chemical and physical UV filters in many cases complement each other, modern sunscreen products frequently resort to combinations comprising both systems. According to the formulated standards for such products, cosmetic sun protection products that are intended to meet the requirements of natural cosmetics must not contain any chemical UV filters. The UV protection of these is exclusively based on the use of physical UV filters.

The ability of sun protection products to prevent UV rays from penetrating into the skin is expressed by the sun protection factor (SPF) thereof. Formerly, this value was determined in in-vivo experiments, in which the occurrence of skin reddening was determined for a defined irradiation amount and duration. However, because inflammatory processes in the skin that are related to skin reddening are triggered rather by the exposure to shorter-wave UV-B rays, this method cannot be employed to determine the degree of protection against UV-A rays. However, because the effect of UV-A rays on the skin, as described above, is no less harmful, in recent times supplemental in-vitro methods were developed for determining UVA absorption, which has remedied this deficiency of the prior art. These are intended to assure that sun protection products have a protective effect over the entire UV range.

For both the chemical UV filters and the inorganic pigments to have an optimal effect, the homogeneous distribution thereof on the skin surface is an important prerequisite. Moreover, a low tendency of the chemical UV filters to penetrate into the skin is of great importance so as to prevent reactions of the excited, frequently radical species in the deeper skin layers. These parameters are controlled primarily by way of the oil components used in the formulation.

In order to produce sunscreen products, a person skilled in the art will therefore use oil components that combine several properties. For example, they must dissolve sun protection filters well for various UV ranges over a wide temperature range, disperse inorganic pigments in a stable manner and, for the purpose of a homogeneous distribution of the sun protection factors on the skin, they must exhibit good spreading ability.

Moreover, further requirements exist for oil components used in modern sun protection products. For example, the cosmetic properties of the formulation play an important role in the continuity of the application of the product by the consumer. The quality of protection against harmful UV radiation is thus also directly related to the user friendliness. Finally, the production of raw materials for dermatological and cosmetic products has become the center of attention over the last few years. To this end, a strong trend toward raw materials from renewable resources has been observed.

It is the object of the invention to provide a preparation of the type mentioned above, which allows for an effective and user-friendly formulation of chemical and/or physical UV filters in these preparations.

Surprisingly, it has been found that esters of a C8-C16 fatty acid and isoamyl alcohol, such as isoamyl laurate, excellently meet these requirements for a series of common chemical and physical UV filters and thus offer a good solution to the challenges in terms of the quality of oil components for sun protection formulations.

The invention relates to a cosmetic or dermatological preparation, comprising:
  a) one or more chemical sun protection filters selected from the group consisting of 2,4,6-trianilino-p-(carbo-2'-ethylhexyl-1'oxy)-1,3,5-triazine (ethylhexyl triazone), 1-(4-tert-butylphenyl)-3-(4-methoxyphenyl)-propane-1,3-dion (butyl methoxydibenzoylmethane), bis-octyloxyphenol-methoxyphenyl-triazine (bis-ethylhexyloxyphenol methoxyphenyl triazine) and 2-[-4-(diethylamino)-2-hydroxybenzoyl]benzoic acid hexylester (diethylamino hydroxybenzoyl hexyl benzoate); and/or one or more sun protection filters selected from the group consisting of superficially treated, or untreated, pigments of titanium dioxide or zinc oxide;
  b) at least one ester of a C8-C16 fatty acid and isoamyl alcohol.

The present invention thus relates to cosmetic and dermatological preparations, in particular sunscreen products, having a content of an ester of a C8-C16 fatty acid and isoamyl alcohol (preferably isoamyl laurate) and one or more chemical UV filters from the group consisting of ethylhexyl triazone, butyl methoxydibenzoylmethane, diethylamino hydroxybenzoyl hexyl benzoate and bis-ethylhexyloxyphenol methoxyphenyl triazine and/or one or more physical UV filters from the group consisting of unmodified or superficially modified zinc oxide and/or titanium dioxide pigments.

From a structural point of view, chemical UV filters are part of the aromatic compound class in which the absorption spectrum was shifted into the wavelength range of UV light by substituents and/or heteroatoms. A challenge in formulating the chemical UV filters is that these are poorly soluble, with a few exceptions, and have a pronounced crystallization tendency. The latter property frequently also results in limited oil solubility, which restricts the usage concentration of chemical UV filters and hence the sun protection factor of the formulation in question.

This problem is compounded by the fact that the absorption maxima of chemical UV filters do not cover the entire range of harmful UV-A and UV-B radiation. This fact frequently necessitates the use of mixtures of UV filters having differing absorption maxima so as to ensure as effective a broad spectrum protection of the skin as possible from the harmful effects of UV radiation by a sunscreen product. Particularly advantageous UV filters that are characterized by good sun protection properties and have been widely used in the recent past include, for example, the UV-B filters 2,4,6-trianilino-p-(carbo-2'-ethylhexyl-1'oxy)-1,3,5-triazine (INCI: ethylhexyl triazone), which is distributed by BASF under the trade name of Uvinul T 150, the UV-A filters 1-(4-tert-butylphenyl)-3-(4-methoxyphenyl)-propane-1,3-dion (INCI: butyl methoxydibenzoylmethane), which is offer by DSM under the trade name of Parsol 1789, for example, or 2-[-4-(diethylamino)-2-hydroxybenzoyl]benzoic acid hexylester (INCI: diethylamino hydroxybenzoyl hexyl benzoate), which is marketed by BASF under the trade name of Uvinul A Plus, as well as bis-octyloxy-phenolmethoxyphenyltriazine (INCI: bis-ethylhexyloxyphenol methoxyphenyl triazine), a broad spectrum filter that is offered, for example, by Ciba Geigy under the trade name of Tinosorb S (EP0775698 B1). A person skilled in the art will know that these UV filters pose particularly high requirements in terms of the dissolving power of the oil components that are employed.

The sun protection effect of the chemical UV filters is complemented by inorganic pigments, such as titanium dioxide or zinc oxide, which in very finely ground form reflect the UV radiation. So as to increase the compatibility thereof with other constituents of sun protection formulations, these pigments are frequently superficially hydrophobized. Oil components that promote the incorporation of such pigments must exhibit advantageous chemical-physical properties. They should, for example, have low surface tension yet high polarity, whereby they have good wettability.

In keeping with the prior art, these requirements are presently satisfied by oils having various structures. The groups of linear alkyl benzoates, esters of 1,3-butylene glycol or 1,3-propylene glycol, and esters of dicarboxylic acids shall be mentioned here by way of example.

From the group of linear alkyl benzoates, C12-15 alkyl benzoate is used widely and offered under the brand name of Finsolv TN or Cetiol AB. While C12-15 alkyl benzoate represents a good option to dissolve the UV filters and disperse pigments, it cannot be produced from renewable resources. Moreover, as compared to other products, it leaves a comparatively fatty film on the skin (L. Rigano, R. Leporatti in *Seifen, Öle, Fette, Wachse [Soaps, Oils, Fats, Waxes]*, 2004, 1/2, 12-22).

The latter disadvantage of the prior art has been solved in part by esters of 1,3-butanediol. EP0860164 B1, for example, describes the use of butylene glycol dicaprylate/dicaprate, which is marketed under the name of Dermofeel® BGC, in combination with the UVB filter ethylhexyl triazone. The application properties of sun protection products containing butylene glycol dicaprylate/dicaprate are described as being advantageous in (L. Rigano, R. Leporatti in *Seifen, Öle, Fette, Wachse*, 2004, 1/2, 12-22). A further ester of 1,3-butanediol is butylene glycol cocoate, the use of which as a wetting agent for pigments is described in EP1807120 B1.

Dibutyl adipate, which is used widely under the name of Cetiol B, shall be mentioned from the group of diesters of dicarboxylic acids.

These aforementioned esters solve the technical requirements with respect to the dissolving and dispersing powers of chemical and physical UV filters well, yet they do not address the requirement of being producible from renewable resources. While they solve some of the disadvantages of the prior art, they are not fully compatible with the ecological requirements of modern raw cosmetic materials.

Surprisingly, and in a way that was not foreseeable to a person skilled in the art, the identification of the aforementioned esters, and more particularly isopentyl laurate (INCI: isoamyl laurate), involves oil components which can be produced from renewable resources and which exhibit good dissolving power for the chemical UV filters, which are ethylhexyl triazone, butyl methoxydibenzoylmethane, diethylamino hydroxybenzoyl hexyl benzoate and bis-ethylhexyloxyphenol methoxyphenyl triazine, reduce the crystallization tendency of the aforementioned UV filters, even in mixtures with other oil components, excellently disperse physical UV filters from the group consisting of the superficially untreated or modified inorganic titanium dioxide or zinc oxide pigments and stabilize them in the formulation, have good spreading ability and hence assure a homogeneous distribution of the aforementioned chemical and physical UV filters on the skin, and which additionally have cosmetically appealing properties, such as fast absorption into the skin, low oiliness and low film formation, and which thereby satisfy the aforementioned technical requirements for the described chemical UV filters and remedy the ecological and economic disadvantages of the prior art.

The present invention therefore relates to cosmetic and dermatological sun protection preparations, and more particularly skin-nourishing cosmetic and dermatological preparations, having a content of the aforementioned esters, such as isoamyl laurate, and one or more chemical UV filters from the group consisting of:

2,4,6-trianilino-p-(carbo-2'-ethylhexyl-1'oxy)-1,3,5-triazine (ethylhexyl triazone)

1-(4-tert-butylphenyl)-3-(4-methoxyphenyl)-propane-1, 3-dion (butyl methoxydibenzoylmethane)

bis-octyloxyphenol-methoxyphenyl-triazine (bis-ethylhexyloxyphenol methoxyphenyl triazine)

2-[-4-(diethylamino)-2-hydroxybenzoyl]benzoic acid hexylester (diethylamino hydroxybenzoyl hexyl benzoate) and/or one or more physical UV filters from the group consisting of superficially untreated or modified inorganic titanium dioxide and/or zinc oxide pigments.

The oil components for sunscreen formulation according to the invention can be obtained from renewable resources, satisfy the technical requirements and have organoleptic properties, which promote the regular use of the sunscreen product.

The invention will be described in more detail hereafter by way of the example of isoamyl laurate as a particularly preferred embodiment, without being limited thereto. Isoamyl laurate can be produced by the esterification of isopentyl alcohol and lauric acid. Both raw materials can be obtained from renewable sources. Other isoamyl esters that can be used according to the invention are notably the esters of isoamyl alcohol with caprylic acid, capric acid, myristic acid and palmitic acid.

Surprisingly it was found that by adding, according to the invention, isoamyl laurate to cosmetic formulations containing the aforementioned UV filters, a comparable amount of these UV filters was dissolved as with butylene glycol diesters or C12-15 alkyl benzoates, yet the formulations, by comparison, are marked by a considerably more appealing skin sensation and good distribution on the skin. They are absorbed quickly into the skin and leave no oil or sticky film behind.

The aforementioned UV filters can be employed in the formulations according to the invention either alone or in combination so as to ensure effective broad spectrum protection. The overall quantity of 2,4,6-trianilino-p-(carbo-2'-ethylhexyl-1'oxy)-1,3,5-triazine (ethylhexyl triazone) is then advantageously selected in a range of 0.1% to 10%, and preferably 0.5 to 6.0%, the overall quantity of 1-(4-tert-butylphenyl)-3-(4-methoxyphenyl)-propane-1,3-dion (butyl methoxydibenzoylmethane) is advantageously selected in the range of 0.1 to 6.0%, and preferably 0.5 to 4.0%, the overall quantity of bis-octyloxyphenol methoxyphenyl triazine (bis-ethylhexyloxyphenol methoxyphenyl triazine) is advantageously selected in the range of 0.1% to 15%, and preferably 0.5 to 10%, and the quantity of 2-[-4-(diethylamino)-2-hydroxybenzoyl]benzoic acid hexylester (diethylamino hydroxybenzoyl hexyl benzoate) is used in the range of 0.1% to 10%, and preferably 0.5 to 6%.

According to the formulated standards for such products, cosmetic sun protection products that are intended to meet the requirements of natural cosmetics must not contain any chemical UV filters, as mentioned above. The UV protection of these is exclusively based on the use of physical UV filters. So as to achieve sufficient sun protection, high concentrations of the titanium dioxide and/or zinc oxide pigments used are required, which in many cases can negatively impact the skin sensation of the formulation. It was surprisingly found that isoamyl laurate was also excellently able to disperse both superficially untreated and superficially modified titanium dioxide and zinc oxide pigments and the resulting formulations according to the invention were marked by considerably improved spreading ability and a more pleasant skin sensation in the direct comparison with other oil components compliant with natural cosmetics.

The aforementioned esters, such as isoamyl laurate, are thus excellently suited both for use in classic sun protection products, in which the effect is based on the use of chemical and physical UV filters, and for use in certified natural cosmetics, in which the sun protection is exclusively based on the effect of inorganic pigments.

The overall quantity of isoamyl esters in formulations according to the invention is 0.1% to 50%, and preferably 0.5% to 20%, relative to the total weight of the formulation. It can be used alone or, of course, in combination with other oil components for dissolving the aforementioned UV filters such as C12-15 alkyl benzoate, butylene glycol dicaprylate/dicaprate or dibutyl adipate. All percentage information in the claims and the specification denotes percent by weight, unless stated otherwise.

The sunscreen formulations according to the invention can be composed in the usual manner and can be used for cosmetic and/or dermatological sun protection, or for the treatment, care and cleansing of the skin and/or hair, or as a cosmetic product.

They may contain cosmetic additives as they are typically used in such formulations, such as further oil components, emulsifiers, pearlizing waxes, consistency regulators, thickening agents, superfattening agents, stabilizing agents, polymers, silicone compounds, fats, waxes, lecithins, phospholipids, active biogenic agents, UV sun protection filters, antioxidants, deodorants, antiperspirants, anti-dandruff substances, film formers, swelling agents, insect repellents, self-tanners, tyrosin inhibitors (depigmentation agents), hydrotropic agents, solubilizers, preservatives, perfume oils, dyes, and the like, which are listed hereafter by way of example.

Oil Components

Personal care products such as creams, lotions and milk typically contain a number of further oil components and emollients, which contribute to further optimizing the organoleptic properties. The oil components are typically present in a total quantity of 0.1 to 50% by weight, preferably 5 to 25% by weight, and more particularly 5 to 15% by weight. Possible oil components are, for example, Guerbet alcohols based on fatty alcohols containing 6 to 18, and preferably 8 to 10 carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, oleyl myristate, oleyl palmitate, oleyl stearate, oleyl isostearate, oleyl oleate, oleyl behenate, oleyl erucate, behenyl myristate, behenyl palmitate, behenyl palmitate [sic], behenyl stearate, behenyl isostearate, behenyl oleate, behenyl behenate, erucyl myristate, erucyl palmitate, erucyl stearate, erucyl isostearate, erucyl oleate, erucyl behenate, and erucyl erucate. In addition, esters of linear $C_6$-$C_{22}$ fatty acids with unbranched or branched polyvalent alcohols, such as butylene glycol dicaprylate/dicaprate (Dermofeel® BGC) or esters of 2-methyl-1,3-propane diol, of 1,1,1-trimethylolethane or 1,1,1-trimethylolpropane are suitable. Also suitable are esters of linear $C_6$-$C_{22}$ fatty acids with branched alcohols, in particular 2-ethyl hexanol, esters of $C_{18}$-$C_{38}$ alkyl hydroxycarboxylic acids with linear or branched $C_6$-$C_{22}$ fatty alcohols, in particular dioctyl malate, esters of linear and/or branched fatty acids with polyvalent alcohols (such as propylene glycol, dimerdiol or trimertriol) and/or Guerbet alcohols, triglycerides based on $C_6$-$C_{10}$ fatty acids, liquid monoglyceride/diglyceride/triglyceride mixtures based on $C_6$-$C_{18}$ fatty acids, esters of $C_6$-$C_{22}$ fatty alcohols and/or Guerbet alcohols with aromatic carboxylic acids, in particular benzoic acid, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonate such as dicaprylyl carbonate (Cetiol® CC), Guerbet carbonates based on fatty alcohols having 6 to 18, and preferably 8 to 10 carbon atoms, esters of benzoic acid with linear and/or branched $C_6$-$C_{22}$ alcohols (such as Finsolv® TN), linear or branched, symmetrical or non-symmetrical dialkyl ethers having 6 to 22 carbon atoms per alkyl group, such as dicaprylyl ether (Cetiol® OE), ring opening products of epoxidized fatty acid esters with polyols, silicone oils (cyclomethicone, silicone methicone types and the like) and/or aliphatic or naphthenic hydrocarbons, such as squalane, squalene or dialkyl cyclohexane.

Emulsifiers

Possible emulsifiers are, for example, non-ionogenic surfactants from at least one of the following groups:

Addition products of 2 to 30 moles ethylene oxide and/or 0 to 5 moles propylene oxide on linear fatty alcohols having 8 to 22 carbon atoms, on fatty acids having 1 to 22 carbon atoms, on alkyl phenols having 8 to 15 carbon atoms in the alkyl group and alkyl amines having 8 to 22 carbon atoms in the alkyl radical Alkyloligoglycosides having 8 to 22 carbon atoms in the alkyl radical and the ethoxylated analogs thereof Addition products of 1 to 15 moles ethylene oxide on castor oil and/or hardened castor oil Addition products of 15 to 60 moles ethylene oxide on castor oil and/or hardened castor oil Partial esters of glycerol and/or sorbitan with unsaturated, linear or saturated, branched fatty acids having 12 to 22 carbon atoms and/or hydroxy carboxylic acids having 3 to 18 carbon atoms and the adducts thereof with 1 to 30 moles ethylene oxide Partial esters of polyglycerol (average self-condensation rate of 2 to 8), polyethylene glycol (relative molar mass 400 to 5000), trimethylol propane, pentaerythrite, sugar alcohols (such as sorbitol), alkyl glucosides (such as methyl glucoside, butyl glucoside, lauryl glucoside) and polyglucosides (such as cellulose) with saturated and/or unsaturated, linear or branched fatty acids having 12 to 22 carbon atoms and/or hydroxy carboxylic acids having 3 to 18 carbon atoms and the adducts thereof with 1 to 30 mole ethylene oxide Mixed esters of pentaerythrite, fatty acids, citric acid and fatty alcohol and/or mixed esters of fatty acids having 6 to 22 carbon atoms, methyl glucose and polyols, preferably glycerol or polyglycerol monoalkyl, dialkyl and trialkyl phosphates and mono-, di- and/or tri-PEG alkyl phosphates and the salts thereof Wool wax alcohols Polysiloxane-polyalkyl-polyether copolymers or the corresponding derivatives Block copolymers such as polyethylene glycol 30 dipolyhydroxy stearate Polymer emulsifiers such as Pemulen types (TR-1, TR-2) by Goodrich and Polyalkylene glycols

Ethylene Oxide Addition Products

The addition products of ethylene oxide and/or of propylene oxide on fatty alcohols, fatty acids, alkyl phenols or on castor oil constitute known, commercially available products. These are mixtures of homologs in which the mean alkoxylation rate corresponds to the ratio of the substance quantities of ethylene oxide and/or propylene oxide and substrate with which the addition reaction is carried out. $C_{12/18}$ fatty acid monoesters and diesters of addition products of ethylene oxide on glycerol are known as moisturizing agents for cosmetic preparations.

Sorbitan Esters

Possible sorbitan esters are sorbitan monoisostearate, sorbitan sesquiisostearate, sorbitan diisostearate, sorbitan triisostearate, sorbitan monooleate, sorbitan sequioleate, sorbitan dioleate, sorbitan trioleate, sorbitan monoerucate, sorbitan sesquierucate, sorbitan dierucate, sorbitan trierucate, sorbitan monoricinolate, sorbitan sesquiricinolate, sorbitan diricinolate, sorbitan triricinolate, sorbitan monohydroxystearate, sorbitan monotartrate, sorbitan sesquitartrate, sorbitan ditartrate, sorbitan tritartrate, sorbitan monocitrate, sorbitan sesquitartrate, sorbitan dicitrate, sorbitan tricitrate, sorbitan monomaleate, sorbitan sesquimaleate, sorbitan dimaleate, sorbitan trimaleate and the technical mixtures thereof. Addition products of 1 to 30, and preferably 5 to 10, moles of ethylene oxide on the aforementioned sorbitan esters are also suitable.

Polyglycerol Esters

Typical examples of suitable polyglycerol esters are polyglyceryl-3 stearates (Dermofeel® PS), polyglycerol-3 palmitates (Dermofeel® PP), polyglyceryl-6 caprylates (Dermofeel® G 6 CY), polyglyceryl-10 laurates (Dermofeel® G 10 L), polyglyceryl-2 laurates (Dermofeel® G 2 L), polyglyceryl-3 laurates (Dermofeel® G 3 L), polyglyceryl-5 laurates (Dermofeel® G 5 L), polyglyceryl-2 dipolyhydroxystearates (Dehymuls® PGPH), polyglycerol-3 diisostearates (Lameform® TGI), polyglyceryl-4 isostearates (Isolan® Gl 34), polyglyceryl-3 methylglucose distearates (Tego Care® 450), polyglyceryl-3 beeswax (Cera Bellina®), polyglyceryl-4 caprates (polyglycerol caprate T2010/90), polyglyceryl-3 cetyl ethers (Chimexane® NL), polyglyceryl-3 distearates (Cremophor® GS 32) and polyglyceryl polyricinoleates (Dermofeel® PR), polyglyceryl dimerate isostearates and the mixtures thereof. Examples of further suitable polyol esters are the monoesters, diesters and triesters of trimethylolpropane reacted optionally with 1 to 30 moles ethylene oxide, or pentaerythrite with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as palmitic acid, stearic acid of behenic acid, as well as dicarboxylic acid having 12 to 22 carbon atoms, such as azelaic acid or sebacic acid.

Amphoteric and Cationic Emulsifiers

Moreover, zwitterionic surfactants can be used as emulsifiers. Zwitterionic surfactants are those surface-active compounds which carry at least one quaternary ammonium group and at least one carboxylate group and a sulfonate group in the molecule. Particularly suitable amphoteric surfactants are those known as betaines such as N-alkyl-N,N-dimethyl ammonium glycinates, for example cocoalkyl dimethyl ammonium glycinate, N-acylamino-propyl-N,N-dimethyl ammonium glycinates, for example cocoacylaminopropyl dimethyl ammonium glycinate, and 2-alkyl-3-carboxymethyl-3-hydroxyethyl imidazolines, each having 8 to 18 carbon atoms in the alkyl or acyl group, and cocoacylaminoethyl hydroxyethylcarboxymethylglycinate. The fatty acid amide derivative known under the CTFA designation of cocoamidopropyl betaine is particularly suited. Ampholytic surfactants are likewise suitable emulsifiers. Ampholytic surfactants are surface-active compounds which, in addition to a $C_{8/18}$ alkyl group or acyl group, contain at least one free amino group and at least one —COOH or —SO$_3$H— group in the molecule and are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycin, N-alkyl taurines, N-alkyl sarcosines, 2-alkylaminopropionic acids and alkylaminoacetic acids, each having approximately 8 to 18 carbon atoms in the alkyl group. Particularly preferred ampholytic surfactants are N-cocoalkylamino propionate, cocoacylaminoethyl aminopropionate and $C_{12/18}$ acylsarcosine. Finally, cation surfactants are also possible emulsifiers, wherein those of the esterquat type, and preferably methyl-quaternized difatty acid triethanolamine ester salts, are particularly preferred.

Fats and Waxes

Fats and waxes are added to personal care products as nourishing ingredients and in order to increase the consistency of the cosmetics. Typical examples of fats are glycerides, which is to say solid or liquid, vegetable or animal products, which substantially contain mixed glycerol esters of higher fatty acids. Fatty acid partial glycerides, which is to say technical monoesters and/or diesters of glycerol with fatty acids having 12 to 18 carbon atoms such as glycerol monolaurate/dilaurate, glycerol palmitate or glycerol stearate may also be used. Possible waxes include natural waxes, such as candelilla wax, carnauba wax, Japan wax, esparto wax, cork wax, guaruma wax, rice germ oil wax, sugar cane wax, ouricury wax, montan wax, bees wax, shellac wax, spermaceit, lanolin (wool wax), preen gland fat, ceresin, ozokerite (mineral wax), petrolatum, paraffin waxes, microcrystalline waxes; chemically modified waxes (hard waxes), such as montan ester waxes, sasol waxes, hydrated jojoba waxes as well as synthetic waxes, such as polyalkylene waxes and polyethylene glycol waxes. In addition to the fats, possible additives include fat-like substances such as lecithins and phospholipds. A person skilled in the art considers the term 'lecithins' to include those glycerophospholids which are formed from fatty acids, glycerol, phosphoric acid and choline by way of esterification. Lecithins are thus also frequently referred to as phosphatidylcholines (PC) in professional circles. Kephalines, which are also referred to as phosphatide acids and constitute derivatives of 1,2-diacyl-sn-glycerol-3-phosphoric acids, shall be mentioned as examples of natural lecithins. In contrast, phospholipids are generally monoesters, and preferably diesters, of phosphoric acid with glycerol (glycerol phosphates), which are included in general in fats. In addition, sphingosines or sphingolipids may be used.

Pearlizing Waxes

Possible pearlizing waxes include: alkylene glycol esters, in particular ethylene glycol distearate; fatty acid alkanol amides, in particular coconut fatty acid diethanol amide; partial glycerides, in particular stearic acid monoglyceride; esters of polyvalent, optionally hydroxy-substituted carboxylic acids with fatty alcohols having 6 to 22 carbon atoms, in particular long-chained esters of tartaric acid; lipids, for example fatty alcohols, fatty ketones, fatty aldehydes, fatty ethers and fatty carbonates, which in total contain at least 24 carbon atoms, in particular laurone and distearyl ether; fatty acids such as stearic acid, hydroxystearic acid or behenic acid, ring opening products of olefin epoxides having 12 to 22 carbon atoms with fatty alcohols having 12 to 22 carbon atoms and/or polyols having 2 to 15 carbon atoms and 2 to 10 hydroxyl groups and the mixtures thereof.

Consistency Regulators and Thickening Agents

Primarily fatty alcohols or hydroxyfatty alcohols having 12 to 22, and preferably 16 to 18, carbon atoms, and additionally partial glycerides, fatty acids or hydroxyfatty acids are possible further consistency regulators. A combination of these substances with alkyl oligoglucosides and/or fatty acid-N-methylglucamides having an identical chain length and/or polyglycerol poly-12-hydroxystearates is preferred. Suitable thickening agents are, for example, Aerosil types (hydrophilic silicic acids), polysaccharides, in particular xanthan gum, guar-guar, agar-agar, alginates and tylose, carboxymethyl cellulose and hydroxyethyl and hydroxypropyl cellulose, additionally higher-molecular-weight polyethylene glycol monoesters and diesters of fatty acids, polyacrylates (such as Carbopole® and Permulen types by Goodrich; Synthalene® by Sigma; Keltrol types by Kelco; Sepigel types by Seppic; or Salcare types by Allied Colloids), polyacrylamides, polymers, polyvinyl alcohol and polyvinylpyrrolidone. Bentonites, such as Bentone® Gel VS-5PC (Rheox), which are a mixture of cyclopentasiloxane, disteardimonium hectorite and propylene carbonate, have found to be particularly effective. In addition, surfactants such as ethoxylated fatty acid glycerides, esters of fatty acids with polyols such as pentaerythrite or trimethylol propane, fatty alcohol ethoxylates with a suitable distribution of homologs or alkyl oligoglucosides as well as electrolytes such as table salt and ammonium chloride are possible.

Superfattening Agents

Superfattening agents that are used may include substances such as lanolin and lecithin as well as polyethoxylated or acylated lanolin and lecithin derivatives, polyol fatty acid esters, monoglycerides and fatty acid alkanol amides, wherein the latter are also used as foam stabilizers.

Stabilizers

Metal salts of fatty acids, such as magnesium-, aluminum- and/or zinc-stearate or -ricinoleate can be used as stabilizers.

Polymers

Suitable cationic polymers include, for example, cationic cellulose derivatives, such as quaternized hydroxyethyl cellulose, which is available under the name of Polymer JR 400® from Amerchol, cationic starch, such as quaternized starches, which are available under the brand names of Amylomer® and Symbio®quat from Dr. Straetmans, copolymers of diallyl ammonium salts and acrylamides, quaternized vinylpyrrolidone/vinilimidazole polymers, such as Luviquat® (BASF), condensation products of polyglycols and amines, quaternized collagen polypeptides, such as lauryldimonium hydroxypropyl hydrolyzed collagen (Lamequat®L/Grünau), quaternized wheat polypeptides, polyethylene imine, cationic silicone polymers, such as amodimethicone, copolymers of adipic acid and dimethylaminohydroxypropyl diethylene triamine (Cartaretine®/Sandoz), copolymers of acrylic acid with dimethyldiallylammonium chloride (Merquat® 550/Chemviron), polyaminopolyamides and the cross-linked water-soluble polymers thereof, cationic chitin derivatives, such as quaternized chitosan, optionally with microcrystalline distribution, condensation products from dihalogen alkylene, such as dibromobutane with bisdialkylamines, such as bis-dimethylamino-1,3-propane, cationic guar-gum, such as Jaguar® CBS, Jaguar® C-17, Jaguar® C-16 by Celanese, and quaternized ammonium salt polymers, such as Mirapol® A-15, Mirapol® AD-1, Mirapol® AZ-1 by Miranol.

Anionic, zwitterionic, amphoteric and non-ionic polymers may be, for example, vinyl acetate/crotonic acid copolymers, vinylpyrrolidone/vinyl acrylate copolymers, vinyl acetate/butyl maleate/isobornyl acrylate copolymers, methyl vinyl ether/maleic acid anhydride copolymers and the esters thereof, non-crosslinked polyacrylic acids and polyacylic acids cross-linked with polyols, acrylamidopropyltrimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinylpyrrolidone/vinyl acetate copolymers, vinylpyrrolidone/dimethylaminoethyl methacrylate/vinyl caprolactam terpolymers, and optionally derivatized cellulose ethers and silicones.

Silicone Compounds

Suitable silicone compounds are, for example, dimethylpolysiloxanes, methylphenylpolysiloxanes, cyclic silicones as well as amino-, fatty acid-, alcohol-, polyether-, epoxy-, fluoro-, glycoside- and/or alkyl-modified silicone compounds, which at room temperature may be present in the liquid or resinous state. Also suitable are simethicones, which are mixtures of dimethicones having an average chain length of 200 to 300 dimethylsiloxane units and hydrogenated silicates.

UV Sun Protection Filters and Antioxidants

In addition to the UV filters according to the invention, further UV filters may be present in the formulations according to the invention. UV-B filters can be oil-soluble or water-soluble. The following oil-soluble substances are mentioned by way of example:

- 3-benzylidene camphor or 3-3-benzylidene norcamphor and the derivatives thereof, such as 3-(4-methylbenzylidene)camphor as described in patent specification EP 0693471 B1.
- 4-aminobenzoic acid derivatives, preferably 4-(dimethylamino)benzoic acid 2-ethylhexyl ester, 4-(dimethylamino)benzoic acid octyl ester and 4-(dimethylamino) benzoic acid 2-amyl ester.
- Esters of cinnamic acid, preferably 4-methoxycinnamic acid 2-ethylhexyl ester, 4-methoxycinnamic acid propyl ester, 4-methoxycinnamic acid isoamyl ester or 2-cyano-3,3-phenylcinnamic acid 2-ethylhexyl ester (octocrylene)
- Esters of salicyclic acid, preferably salicylic acid 2-ethylhexyl ester, salicylic acid 4-isopropylbenzyl ester or salicylic acid homomenthyl ester
- Derivatives of bezophenone, preferably 2-hydroxy-4-methoxybezophenone, 2-hydroxy-4'-methoxybezophenone, 2,2'-dihydoxy-4-methoxybenzophenone
- Esters of benzalmalonic acid, preferably 4-methoxybenzmalonic acid di-2-ethylhexyl ester
- Triazine derivatives such as dioctyl butamido triazone (Uvasorb HEB)
- Ketotricyclo(5.2.1.0)decane derivatives, as described in EP 0694521 B1.

Possible water-soluble substances are:

- 2-phenylbenzimidazole-5-sulfonic acid and the alkali, alkaline earth, ammonium, alkylammonium, alkanolammonium and glucammonium salts thereof
- Sulfonic acid derivatives of benzophenone, preferably 2-hydroxy-4-methoxybenzophenone-5-sulfonic acid and the salts thereof
- Sulfonic acid derivatives of benzylidene camphor, such as 4-(2-oxo-3-bornylidene methyl)benzolsulfonic acid and 2-methyl-5-(2-oxo-3-bornylidene)sulfonic acid and the salts thereof.

Especially derivatives of benzoylmethane are typical UV-A filters, for example 1-phenyl-3-(4'isopropylphenyl)-propane-1,3-dion and enamine compounds, as described in DE 19712033 A1. The UV-A and UV-B filters can also be used in the form of mixtures, of course. Advantageously, such combinations are combined with water-soluble filters such as 2-phenylbenzimidazole-5-sulfonic acid and the akali, alkaline earth, ammonium, alkylammonium, alkanolammonium and glucammonium salts thereof.

In addition to the aforementioned soluble substances, insoluble sun protection pigments, which is to say finely dispersed metal oxides and salts, may be used for this purpose. Examples of suitable metal oxides include in particular titanium dioxide and zinc oxide, and oxides of iron, zirconium, silicone, manganese, aluminum and cerium, as well as the mixtures thereof. Silicates (talc), barium sulfate or zinc stearate can be used as salts. The oxides and salts are employed in the form of pigments for skin-nourishing and skin-protecting emulsions in cosmetics products. The particles should have a mean diameter of less than 100 nm, preferably between 5 and 50 nm, and more particularly between 15 and 30 nm. They can have a spherical shape, however, it is also possible to employ particles that have an ellipsoid shape or a shape deviating from the spherical shape in another manner. The pigments can also be present in surface-treated form, which is to say in hydrophilized or hydrophobized form. Typical examples include coated titanium dioxides, such as titanium dioxide T 805 by Degussa or Eusolex T 2000 by Merck. Notably silicones, and more particularly trialkoxyoctyl silanes or simethicones are used as hydrophobic coating agents. Sunscreen products preferably contain what is known as micro-pigments or nano-pigments. Micronized zinc oxide is preferred.

In addition to the two aforementioned groups of primary sun protection agents, it is also possible to use secondary sun protection agents of the antioxidant type, which interrupt the photochemical reaction chain that is triggered when harmful UV radiation penetrates into the skin. Typical examples include amino acid (such as histidine, tyrosine or tryptophan) and the derivatives thereof, imidazoles (such as urocanic acid) and the derivatives thereof, peptides such as D,L-carnosine, D-carnosine, L-carnosine and the derivatives thereof, carotinoids, carotenes (such as $\alpha$-carotene, $\beta$-carotene, lycopene) and the derivatives thereof, lipoic acids and the derivatives thereof (such as dihydrolipoic acid), aurothioglucose, propylthiouracil and other thiols (such as thioredoxin, glutathione, cysteine, cystine, cysteamine and the glycolsyl, N-acetyl, methyl, ethyl, propyl, amyl, butyl, lauryl, palmitoyl, oleyl, $\gamma$-linoleyl, cholesteryl and glyceryl esters thereof) and the salts thereof, dilaurylthiodipropionate, distearylthiodipropionate, thiodipropionic acid and the derivatives thereof (esters, ethers, peptides, lipids, nucleotides, nucleosides and salts) as well as sulfoximine compounds (such as buthionine sulfoximine, homocysteine sulfoximine, butionine sulfoximine, penta-, hexa-, hepta-thionine sulfoximine) in very low, tolerable doses (such as pmol to mol), moreover complexing agents such as $\alpha$-hydroxy fatty acids, palmitic acid, phytic acid, lactoferrin), $\alpha$-hydroxy acids (such as citric acid, lactic acid, malic acid), humic acid, bile acid, bile extracts, bilirubin, biliverdin, EDTA, EGTA and the derivatives thereof, unsaturated fatty acids and the derivatives thereof (such as $\gamma$-linolenic acid, linolic acid, oleic acid), folic acid and the derivatives thereof, ubiquinone and ubiquinol and the derivatives thereof, Vitamin C and derivatives (such as ascorbyl palmitate, magnesium ascorbyl phosphate, ascorbyl acetate), tocopherols (such as $\alpha$-tocopherol, $\beta$-tocopherol, $\gamma$-tocopherol, $\delta$-tocopherol) and the derivatives thereof (tocopherol acetate), Vitamin A and derivatives (Vitamin A palmitate) as well as coniferyl benzoate of benzoin, rutinic acid and the derivatives thereof, $\alpha$-glycosyl rutin, ferulic acid, furfurylidene gluticol, carnosine, butylhydroxytoluene, butylhydroxyanisol, nordihydroguaiac acid, nordihydroguaiaretic acid, trihydroxybutyrophenone, uric acid and the derivatives thereof, mannose and the derivatives thereof, superoxide dismutase, zinc and the derivatives thereof ($ZnO$, $ZnSO_4$), selenium and the derivatives thereof (such as selenium methionine), stilbenes and the derivatives thereof (such as stilbene oxide, trans-stilbene oxide) and the derivatives suitable according to the invention (salts, esters, ethers, sugar, nucleotides, nucleosides, peptides and lipids) of the aforementioned active ingredients.

Active Biogenic Agents

Active biogenic agents shall be understood to mean, for example, tocopherol, tocopherol acetate, tocopherol palmitate, ascorbic acid, (deoxy)ribonucleic acid and the fragmentation products thereof, $\beta$-glucans, retinol, bisabolol, allantoin, phytantriol, panthenol, AHA acids, amino acids, ceramides, pseudoceramides, essential oils, plant extracts such as prunus extract, Bambara groundnut extract and vitamin complexes.

Deodorants and Antimicrobial Agents

Cosmetic deodorants counteract, mask or eliminate body odors. Body odors develop as a result of the action of skin bacteria on apocrine sweat, whereby unpleasantly smelling decomposition products are formed. Deodorants therefore contain active ingredients that act as antimicrobial agents, enzyme inhibitors, odor absorbers or odor masking agents.

Antimicrobial Agents

In principle all substances that are effective against gram-positive bacteria are suitable as antimicrobial agents, such as 4-hydroxybenzoic acid and the salts and esters thereof, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)-phenol, 2-benzyl-4-chlorophenol, 3-(4-chlorophenoxy)-1,2-propane diol, 3-iodo-2-propinylbutyl carbamate, chlorohexidine, 3,4,'-trichlorocarbanilide (TTC), antibacterial scents, thymol, thyme oil, eugenol, clove oil, menthol, mint oil, farnesol, phenoxyethanol, glycerol monocaprinate, glycerol monocaprylate, glycerol monolaurate (GML), diglycerol monocaprinate (DGMC), salicylic acid N-alkyl amides such as salicylic acid n-octyl amide or salicylic acid n-decyl amide.

Enzyme Inhibitors

Esterase inhibitors, for example, are suitable enzyme inhibitors. These are preferably trialkyl citrates such as trimethyl citrate, tripropyl citrate, triisopropyl citrate, tributyl citrate and in particular triethyl citrate (Hydagen® CAT). The substances inhibit enzyme activity and thus reduce the formation of odors. Further substances that can be used as esterase inhibitors include sterol sulfates or phosphates, such as lanosterol, cholesterol, campesterol, stigmasterol and sitosterol sulfate or phosphate, dicarboxylic acids and the esters thereof, such as glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and the esters thereof, such as citric acid, malic acid, tartaric acid or tartaric acid diethyl ester, as well as zinc glycinate.

Odor Absorbers

Substances that are able to absorb and substantially retain odor-forming compounds are suitable odor absorbers. They lower the partial pressure of the individual components and thereby also reduce the propagation velocity thereof. The key here is that perfume agents must remain unimpaired. Odor absorbers are not effective against bacteria. The main constituent they contain is, for example, a complex zinc salt of ricinoleic acid or special, substantially odor-neutral fragrances, which are known to a person skilled in the art as "fixatives", such as extracts of labdanum or styrax or certain abietic acid derivatives. Odor-masking agents are scents or perfume oils which, in addition to the function thereof as odor-masking agents, lend the deodorants their respective fragrances. Perfume oils include, for example, mixtures of natural and synthetic scents. Natural scents are extracts of blossoms, stems and leaves, fruits, fruit peels, roots, timbers, herbs and grasses, needles and twigs as well as resins and balsams. In addition, raw animal products may be used, for example cibet and castoreum. Typical synthetic scent compounds are products of the ester, ether, aldehyde, ketone, alcohol and hydrocarbon types. Ester-type scent compounds are, for example, benzyl acetate, p-tert.-butylcyclohexyl acetate, linalyl acetate, phenylethyl acetate, linalyl benzoate, benzyl formate, allyl cyclohexyl propionate, styrallyl propionate, and benzyl salicylate. The ethers include, for example, benzyl ethyl ethers, the aldehydes include, for example, linear alkanals having 8 to 18 carbon atoms, citral, citronellal, citronellyl oxyacetaldehyde, cyclamen aldehyde, hydroxy citronellal, lilial and Bourgeonal, the ketones include, for example, ionones and methyl cedryl ketone, the alcohols include anethole, citronellol, eugenol, isoeugenol, geraniol, linalool, phenylethyl alcohol and terpineol, and the hydrocarbons primarily include terpenes and balsams. Preferred, however, are mixtures comprising various scents, which together produce an appealing fragrance. In addition, low-volatility essential oils, which are typically used as aroma components, are suitable as perfume oils, for example sage oil, chamomile oil, clove oil, melissa oil, mint oil, cinnamon leaf oil, lime blossom oil, juniper berry oil, vetiver oil, olibanum oil, galbanum oil, labdanum oil, and lavandin oil. Preferred are bergamot oil, dihydromyrcenol, lilial, lyral, cintronellol, phenylethyl alcohol, hexyl cinnamaldehyde, geraniol, benzyl acetate, cyclamen aldehyde, linalool, boisambrene forte, ambroxan, indole, hedione, sandelice, lemon oil, mandarin orange oil, orange oil, allyl amyl glycolate, cyclovertal, lavandin oil, muscatel sage oil, β-damascenone, Geranium Bourbon oil, cyclohexylsalicylate, Vertofix Coeur, Iso E super, Fixolide NP, evernyl, iraldeine gamma, phenyl acetic acid, geranyl acetate, benzyl acetate, rose oxide, Romilat, Irotyl and Floramat, either alone or in mixtures.

Antiperspirants

Antiperspirants reduce sweating by influencing the activity of the eccrine perspiratory glands and thereby counteract underarm perspiration and body odor. Aqueous or anhydrous formulations of antiperspirants typically contain the following ingredients:

Astringent active agents
Oil components
Non-ionic emulsifiers
Co-emulsifiers
Consistency regulators
Additives such as thickeners or complexing agents and/or
non-aqueous solvents such as ethanol, propylene glycol and/or glycerol.

Especially salts of aluminum, zirconium or zinc are suitable astringent active ingredients for antiperspirants. Suitable antihydrotically effective active ingredients are, for example, aluminum chloride, aluminum chlorohydrate, aluminum dichlorohydrate, aluminum sesquichlorohydrate and the complex compounds thereof, for example with propylene glycol-1,2; aluminum hydroxyallantoinate, aluminum chloride tartrate, aluminum zirconium trichlorohydrate, aluminum zirconium tetra-chlorohydrate, aluminum zirconium pentachlorohydrate and the complex compounds thereof, for example with amino acids such as glycine. In addition, antiperspirants may contain small quantities of common oil-soluble and water-soluble additives. Such oil-soluble additives can be, for example:

anti-inflammatory, skin-protecting or fragrant essential oils
synthetic skin-protecting active ingredients and/or
oil-soluble perfume oils.

Common water-soluble additives are, for example, preservatives, water-soluble scents, pH value adjusting agents such as buffer mixtures, water-soluble thickeners such as water-soluble natural or synthetic polymers, for example xanthan gum, hydroxyethyl cellulose, polyvinylpyrrolidone or high-molecular-weight polyethylene oxides.

Film Formers

Conventional film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose and starch derivatives, collagen, hyaluronic acid or the salts thereof and similar compounds.

Swelling Agents

Suitable swelling agents for aqueous phases can be montmorillonite, clay minerals, Pemulen, and alkyl-modified Carbopol types (Goodrich). Additional suitable polymers or swelling agents are shown in the overview by R. Lochhead in Cosm. Toil. 108, 95 (1993).

Insect Repellants

Possible insect repellants are, for example, N,N-diethyl-m-toluamide, 1,2-pentane diol or 3-(N-n-butyl-N-acetyl-amino)-propionic acid ethyl ester), which is sold under the name of Insect Repellent® 3535 by Merck KGaA, as well as butylacetylaminopropionate.

Self-Tanners and Depigmentation Agents

Dihydroxyacetone and erythrulose are suitable self-tanners. Possible tyrosin inhibitors, which prevent the formation of melanin and are used in depigmentation agents, include Arbutin, ferulic acid, kojic acid, coumaric acid and ascorbic acid (Vitamin C).

Hydrotropic Agents

So as to improve the flow behavior, hydrotropic agents may also be used, for example ethanol, isopropyl alcohol or polyols. Polyols that may be considered here preferably contain 2 to 15 carbon atoms and at least two hydroxyl groups. The polyols may contain additional functional groups, in particular amino groups, or can be modified with nitrogen.

Typical examples are:

Glycerol alkylene glycols such as ethylene glycol, diethylene glycol, propylene glycol, butylene glycol, pentylene glycol, hexylene glycol, 1,2-hexane diol and caprylyl glycol as well as polyethylene glycols having an average molecular weight of 100 to 1,000 daltons.

technical oligoglycerol mixtures having a self-condensation rate of 1.5 to 10, such as technical diglycerol mixtures having a diglycerol content of 40 to 50% by weight methylol compounds, in particular trimethylol ethane, trimethylol propane, trimethylol butane, pentaerythrite and dipentarythrite low alkyl glucosides, in particular those having 1 to 8 carbon atoms in the alkyl radical, such as methyl and butyl glucoside sugar alcohols having 5 to 12 carbon atoms, such as sorbitol or mannitol sugars having 5 to 12 carbon atoms, such as glucose or saccharose amino sugar, such as glucosamine dialcohol amines, such as diethanol amine or 2-amino-1,3-propane diol Preservatives Suitable preservatives are, for example, phenoxyethanol, parabens, pentane diol or sorbic acid as well as the additional substance classes listed in Attachment 6, Parts A and B of the Cosmetics Regulation.

Perfume Oils and Aromas

Perfume oils include, for example, mixtures of natural and synthetic scents. Natural scents include extracts of blossoms (lily, lavender, roses, jasmine, neroli, ylang-ylang), stems and leaves (geranium, patchouli, Petitgrain), fruits (anise, coriander, caraway, juniper), fruit peels (bergamot, lemon, orange), roots (Mace, angelica, celery, cardamom, costus, iris, calmus), timbers (pine, sandalwood, guaiac wood, cedar, rosewood), herbs and grasses (tarragon, lemon grass, sage, thyme), needles and twigs (spruce, fir, pine, dwarf pine), resins and balsams (galbanum, elemi, benzoin, myrrh, olibanum, opoponax). In addition, raw animal products may be used, for example cibet and castoreum. Typical synthetic scent compounds are products of the ester, ether, aldehyde, ketone, alcohol and hydrocarbon types. Ester-type scent compounds are, for example, benzyl acetate, phenoxyethyl isobutyrate, p-tert.-butylcyclo-hexyl acetate, linalyl acetate, dimethylbenzyl carbinyl acetate, phenylethyl acetate, linalyl benzoate, benzyl formate, ethylmethylphenyl glycinate, allyl cyclohexyl propionate, styrallyl propinonate, and benzyl salicylate. The ethers include, for example, benzyl ethyl ethers, the aldehydes include, for example, linear alkanals having 8 to 18 carbon atoms, citral, citronellal, citronellyl oxyacetaldehyde, cyclamen aldehyde, hydroxy citronellal, lilial and Bourgeonal, the ketones include, for example, ionones, α-isomethyl ionone and methyl cedryl ketone, the alcohols include citronellol, eugenol, isoeugenol, geraniol, linalool, phenylethyl alcohol, 3-phenyl-1-propanol and terpineol, and the hydrocarbons primarily include terpenes and balsams. However it is preferred to use mixtures comprising various scents, which together produce an appealing fragrance. In addition, low-volatility essential oils, which are typically used as aroma components, are suitable as perfume oils, for example sage oil, chamomile oil, clove oil, melissa oil, mint oil, cinnamon leaf oil, lime blossom oil, juniper berry oil, vetiver oil, olibanum oil, galbanum oil, labdanum oil, and lavandin oil. Preferred are bergamot oil, dihydromyrcenol, lilial, lyral, cintronellol, phenylethyl alcohol, α-hexyl cinnamaldehyde, geraniol, benzyl acetate, cyclamen aldehyde, linalool, boisambrene forte, ambroxan, indole, hedione, sandelice, lemon oil, mandarin orange oil, orange oil, allyl amyl glycolate, cyclovertal, lavandin oil, muscatel sage oil, α-damascenone, Geranium Bourbon oil, cyclohexylsalicylate, Vertofix Coeur, Iso E super, Fixolide NP, evernyl, iraldeine gamma, phenyl acetic acid, geranyl acetate, benzyl acetate, rose oxide, Romilat, Irotyl and Floramat, either alone or in mixtures.

Possible aromas include peppermint oil, curled mint oil, anise oil, star anise oil, caraway oil, eucalyptus oil, fennel oil, lemon oil, wintergreen oil, clove oil, menthol, and the like.

Scent and aroma agents from the group of organic acids, such as p-anise acid, 4-oxopentane acid or cinnamic acid can also be used to impart fragrance to the formulations according to the invention. These may also contribute to the microbiological stabilization of the formulations.

Dyes

The dyes that are used can be substances that are suitable and approved for cosmetic purposes. Examples include Cochineal Red A (C.I. 16255), Patent Blue V (C.I. 42051), Indigot Carmine (C.I. 73015), Chlorophyllin (C.I. 75810), Quinoline Yellow (C.I. 47005), Titanium dioxide (C.I. 77891), Indanthrene blue RS (C.I. 69800) and Alizarin (C.I. 58000). Luminol may also be present as a luminescence dyestuff. These dyes are typically used in concentration of 0.001 to 0.1% by weight, relative to the total mixture.

Three exemplary embodiments of the invention will be explained hereafter.

1. PEG-Free O/W—Sunscreen Lotion

| Phase | Raw materials | INCI | Supplier | % |
|---|---|---|---|---|
| A | Deionized water | Aqua | | up to 100 |
| | Dermofeel PA-3 | Sodium Phytate, Aqua | Dr. Straetmans | 0.10 |
| | Glycerol | Glycerin | | 3.50 |
| | Dermosoft LP | Caprylyl Glycol, Glycerin, Glyceryl Caprylate, Phenylpropanol | Dr. Straetmans | 1.00 |

| Phase | Raw materials | INCI | Supplier | % |
|---|---|---|---|---|
| A1 | Cosmedia SP | Sodium Polyacrylate | Cognis | 0.20 |
|  | Dermofeel GSC | Glyceryl Stearate Citrate | Dr. Straetmans | 2.50 |
| B | Dermofeel sensolv | Isoamyl Laurate | Dr. Straetmans | 8.00 |
|  | Cutina GMS | Glyceryl Stearate | Cognis | 2.00 |
|  | Lanette O | Cetearayl Alcohol | Cognis | 1.00 |
|  | Cetiol B | Dibutyl Adipate | Cognis | 5.00 |
|  | Neo Heliopan AV | Ethylhexyl methoxycinnamate | Symrise | 5.00 |
|  | Parsol 1789 | Butyl Methoxydibenzoylmethane | DSM | 3.00 |
|  | Tinosorb S | Bis-Ethylhexyloxyphenol methoxyphenyl Triazione | Ciba | 3.00 |
|  | Uvinul T150 | Ethylhexyl Triazone | BASF | 3.00 |
| C | DC 246 Fluid | Cyclohexasiloxane, Cyclopentasiloxane | Dow Corning | 2.00 |
| D | Perfume Oil Sugar Ray DH10316 | Perfume | Symrise | 0.20 |
|  | Tinosorb M | Methylene Bis-Benzotriazoyl Tetramethylbutylphenol | Ciba | 4.00 |
|  | Sodium Hydroxide | Sodium Hydroxide |  | 0.13 |

Production: Heat phase A to 80° C. Add A1 and disperse homogeneously using the Ultra Turrax. Heat phase B to 78° C. Stir phase B into phase A while stirring, then homogenize approx. 1 minute using the Ultra Turrax. Cool to approx. 60° C. and add phase C. Cool further, to room temperature, while stirring and add phase D.

2. Natural Sun W/O

| Phase | Raw materials | INCI | Supplier | % |
|---|---|---|---|---|
| A | Tap Water | Aqua |  | up to 100 |
|  | Glycerol | Glycerin |  | 7.00 |
|  | Zinc sulfate Heptahydrate | Zinc Sulfate | Merck | 1.00 |
| B | Dermofeel PR | Polyglyceryl-3 Polyricinoleate | Dr. Straetmans | 5.00 |
|  | Dermosoft GMC | Glyceryl Caprate | Dr. Straetmans | 0.50 |
|  | Dermofeel PO | Glyceryl Oleate | Dr. Straetmans | 1.00 |
|  | Dermofeel sensolv | Isoamyl Laurate | Dr. Straetmans | 10.00 |
|  | Dermofeel MCT | Tricaprylin | Dr. Straetmans | 15.00 |
|  | Cutina HR | Hydrogenated Castor Oil |  | 0.25 |
|  | Bees wax 8104, white, pure | Cera Alba | Kahl & Co | 0.25 |
|  | Emprove | Magnesium Stearate | Merck | 0.50 |
|  | alpha Bisalolol, nat. | Bisabolol | GfN | 0.10 |
|  | Dermofeel Toco 70 non-GMO | Tocopherol | Dr. Straetmans | 0.20 |
| B1 | Zinc Oxide | Zinc Oxide | BASF | 5.00 |
|  | Uv-Titan M160 | Titanium Dioxide | Kemira | 4.6 |
| C | Perfume Oil Sugar Ray DH10316 | Perfume | Frey & Lau | 0.2 |

Production: Heat phase A to 80° C. Heat phase B to 80° C. Disperse phase B1 in phase B. Slowly add phase A to phase B while stirring, then homogenize for 2-5 minutes using the Ultra Turrax. Cool to 32° C. while stirring and add phase C. Cool further to room temperature.

3. Anti Aging Light Day Care Cream SPF 10

| Phase | Raw materials | INCI | Supplier | % |
|---|---|---|---|---|
| A | Deionized water | Aqua |  | up to 100 |
|  | Glycerol | Glycerin |  | 3.00 |
|  | Dermofeel PA-3 | Sodium Phytate | Dr. Straetmans | 0.10 |
|  | Dermosoft LP | Caprylyl Glycol, Glycerin, Glyceryl Caprylate, Phenylpropanol | Dr. Straetmans | 0.80 |
| A1 | Cosmedia SP | Sodium Polyacrylate | Cognis | 0.20 |
|  | Keltrol RD | Xanthan Gum | CP Kelco | 0.30 |
| B | Symbiomuls GC | Glyceryl Stearate Citrate, Cetearyl Alcohol, Glyceryl Caprylate | Dr. Straetmans | 5.00 |
|  | Cetiol SB 45 | Shea Butter | Cognis | 2.50 |
|  | Phytosqualane | Squalane |  | 5.00 |
|  | Dermofeel sensolv | Isoamyl Laurate | Dr. Straetmans | 8.00 |
|  | DC 345 | Cyclopentasiloxane, Cyclohexasiloxane | Dow Corning | 3.00 |
|  | DC 200 | Dimethicone | Dow Corning | 1.00 |
|  | Uvinul A plus | Diethylamino Hydroxybenzoyl Hexyl Benzoate | BASF | 2.80 |
|  | Uvinul MC 80 | Ethylhexyl methoxycinnamate | BASF | 5.20 |
|  | Dermofeel E74 A | Tocopherol Acetate | Dr. Straetmans | 0.50 |
| C | Sculptessence | Water, Glycerin, Linum Usitatissimum Seed Extract | Lucas Meyer Cosmetics | 4.00 |

-continued

| Phase | Raw materials | INCI | Supplier | % |
|---|---|---|---|---|
| D | Mamaku Vital essence | Water, Cyathea medullaris leaf extract | Lucas Meyer Cosmetics | 2.00 |
| | PC Panther (flowery, fruity, fresh) Sensitizer free P0261246 | Perfume | Frey & Lau | 0.30 |
| | Sodium Hydroxide | Sodium Hydroxide | | 0.25 |

Production: Heat phase A to 78° C. and disperse phase A1 in. Heat phase B to 78° C. While stirring, add phase B to phase A and then homogenize for 1-2 minutes using the Ultra Turrax. Cool emulsion while stirring at average speed and add phase C and phase D at less than 40° C.

The invention claimed is:

1. A cosmetic or dermatological preparation, characterized by comprising:
   a) one or more chemical sun protection filters selected from the group consisting of 2,4,6-trianilino-p-(carbo-2'-ethylhexyl-1'oxy)-1,3,5-triazine (ethylhexyl triazone), 1-(4-tert-butylphenyl)-3-(4-methoxyphenyl)-propane-1,3-dion (butyl methoxydibenzoylmethane), bis-octyloxyphenol-methoxyphenyl-triazine (bis-ethylhexyloxyphenol methoxyphenyl triazine) and 2-[-4-(diethylamino)-2-hydroxybenzoyl]benzoic acid hexylester (diethylamino hydroxybenzoyl hexyl benzoate); and/or one or more sun protection filters selected from the group consisting of superficially treated, or untreated, pigments of titanium dioxide or zinc oxide, wherein the preparation comprises 2 to 10% of said titanium dioxide or zinc oxide pigments;
   b) at least one ester of a C8-C16 fatty acid and isoamyl alcohol.

2. The preparation according to claim 1, characterized in that the fatty acid is lauric acid.

3. The preparation according to claim 1, characterized by comprising the ester of a C8-C16 fatty acid and isoamyl alcohol in a concentration of 0.1 to 50%.

4. The preparation according to claim 1, characterized by comprising the ester of a C8-C16 fatty acid and isoamyl alcohol in a concentration of 0.5 to 20%.

5. The preparation according to claim 1, characterized by further comprising 2,4,6-trianilino-p-(carbo-2'-ethylhexyl-1'oxy)-1,3,5-triazine (ethylhexyl triazone) in a concentration of 0.1% to 10%.

6. The preparation according to claim 1, characterized by further comprising 2,4,6-trianilino-p-(carbo-2'-ethylhexyl-1'oxy)-1,3,5-triazine (ethylhexyl triazone) in a concentration of 0.5% to 6.0%.

7. The preparation according to claim 1, characterized by further comprising 1-(4-tert-butylphenyl)-3-(4-methoxyphenyl)-propane-1,3-dion (butyl methoxydibenzoylmethane) in a concentration of 0.1% to 6.0%.

8. The preparation according to claim 1, characterized by further comprising 1-(4-tert-butylphenyl)-3-(4-methoxyphenyl)-propane-1,3-dion (butyl methoxydibenzoylmethane) in a concentration of 0.5% to 4.0%.

9. The preparation according to claim 1, characterized by further comprising bis-octyloxyphenol-methoxyphenyl-triazine (bis-ethylhexyloxyphenol methoxyphenyl triazine) in a concentration of 0.1% to 15.0%.

10. The preparation according to claim 1, characterized by further comprising bis-octyloxyphenol-methoxyphenyl-triazine (bis-ethylhexyloxyphenol methoxyphenyl triazine) in a concentration of 0.5% to 10.0%.

11. The preparation according to claim 1, characterized by further comprising 2-[-4-(diethylamino)-2-hydroxybenzoyl] benzoic acid hexyl ester (diethylamino hydroxybenzoyl hexyl benzoate) in a concentration of 0.1% to 10%.

12. The preparation according to claim 1, characterized by further comprising 2-[-4-(diethylamino)-2-hydroxybenzoyl] benzoic acid hexyl ester (diethylamino hydroxybenzoyl hexyl benzoate) in a concentration of 0.5 to 6%.

* * * * *